(12) United States Patent  
Ostlin et al.

(10) Patent No.: US 7,295,320 B2
(45) Date of Patent: Nov. 13, 2007

(54) DETECTOR ARRANGEMENT BASED ON SURFACES PLASMON RESONANCE

(75) Inventors: Henrik Ostlin, Uppsala (SE); Lars Eriksson, Haninge (SE); Magnus Ljungstrom, Uppsala (SE); Tomas Agren, Uppsala (SE)

(73) Assignee: Gyros AB, Uppsala (SE)

( * ) Notice: Subject to any disclaimer, the term of this patent is extended or adjusted under 35 U.S.C. 154(b) by 522 days.

(21) Appl. No.: 10/999,532

(22) Filed: Nov. 30, 2004

(65) Prior Publication Data

US 2005/0179901 A1 Aug. 18, 2005

Related U.S. Application Data

(63) Continuation of application No. PCT/SE03/00876, filed on May 28, 2003.

(60) Provisional application No. 60/385,179, filed on May 31, 2002.

(30) Foreign Application Priority Data

May 31, 2002 (SE) .................................. 0201657

(51) Int. Cl.
*G01N 21/55* (2006.01)
(52) U.S. Cl. ...................................... 356/445
(58) Field of Classification Search ............... None
See application file for complete search history.

(56) References Cited

U.S. PATENT DOCUMENTS 5,376,252 A 12/1994 Ekstrom
5,384,028 A 1/1995 Ito (Continued)

FOREIGN PATENT DOCUMENTS

JP 11-304693 11/1999
WO WO-0046589 8/2000
WO WO-03102559 12/2003

OTHER PUBLICATIONS

U.S. Appl. No. 10/867,893, Derand et al.

(Continued)

*Primary Examiner*—Gregory J. Toatley, Jr.
*Assistant Examiner*—Juan D Valentin, II
(74) *Attorney, Agent, or Firm*—Fulbright & Jaworski, LLP

(57) ABSTRACT

A detector arrangement, which comprises a rotatable microfluidic disc and a spectrophotometric detector unit. The arrangement is characterized in that the detector unit is based on surface plasmon resonance (SPR) and is capable of measuring an analyte within the detection microcavities, each of which is part of a microchannel structure.

A microfluidic disc having an axis of symmetry and comprising microchannel structures, each of which has an upstream functional part that is at a shorter radial position than a downstream functional part. The disc is characterized in that there are detection microcavities (DMCs) in at least a part of said microchannel structures, and that each of said DMCs has an SPR surface on an inner wall and a detection detection window extending from the SPR surface to the surface of the disc.

The use of the detector arrangement and microfluidic disc described above for determining: a) if the content in one or more of the DMCs is a liquid or a solid state or a gas, and/or b) a feature of an analyte that may be present in a liquid which is present in one or more of the DMCs.

18 Claims, 10 Drawing Sheets

U.S. PATENT DOCUMENTS

| | | | |
|---|---|---|---|
| 5,442,448 A * | 8/1995 | Knoll | 356/445 |
| 5,690,841 A | 11/1997 | Elderstig | |
| 5,773,488 A | 6/1998 | Allmer | |
| 5,962,081 A | 10/1999 | Ohman | |
| 5,994,150 A | 11/1999 | Challener et al. | |
| 5,995,209 A | 11/1999 | Ohman | |
| 6,126,765 A | 10/2000 | Ohman | |
| 6,144,447 A | 11/2000 | Ohman | |
| 6,192,768 B1 | 2/2001 | Wallman | |
| 6,203,291 B1 | 3/2001 | Stemme | |
| 6,300,141 B1 | 10/2001 | Segal et al. | |
| 6,322,682 B1 | 11/2001 | Arvidsson | |
| 6,338,820 B1 | 1/2002 | Hubbard et al. | |
| 6,454,970 B1 | 9/2002 | Ohman | |
| 6,620,478 B1 | 9/2003 | Ohman | |
| 6,632,656 B1 | 10/2003 | Thomas | |
| 6,653,625 B2 | 11/2003 | Andersson | |
| 6,717,136 B2 | 4/2004 | Andersson | |
| 6,728,644 B2 | 4/2004 | Bielik et al. | |
| 6,750,968 B2 * | 6/2004 | Sandusky | 356/445 |
| 6,811,736 B1 | 11/2004 | Ohman | |
| 6,812,456 B2 | 11/2004 | Andersson | |
| 6,812,457 B2 | 11/2004 | Andersson | |
| 6,885,454 B2 * | 4/2005 | Naya et al. | 356/445 |
| 6,924,893 B2 * | 8/2005 | Oldenbourg et al. | 356/369 |
| 2003/0044322 A1 | 3/2003 | Andersson | |
| 2003/0053934 A1 | 3/2003 | Andersson | |
| 2003/0054563 A1 | 3/2003 | Ljungstrom | |
| 2003/0082075 A1 | 5/2003 | Agren | |
| 2003/0094502 A1 | 5/2003 | Andersson | |
| 2003/0129360 A1 | 7/2003 | Derand | |
| 2003/0156763 A1 | 8/2003 | Soderman | |
| 2003/0211012 A1 | 11/2003 | Bergstrom | |
| 2003/0213551 A1 | 11/2003 | Derand | |
| 2003/0231312 A1 | 12/2003 | Sjoberg | |
| 2004/0058408 A1 | 3/2004 | Thomas | |
| 2004/0096867 A1 | 5/2004 | Andersson | |
| 2004/0099310 A1 | 5/2004 | Andersson | |
| 2004/0120856 A1 | 6/2004 | Andersson | |
| 2004/0202579 A1 | 10/2004 | Larsson et al. | |

OTHER PUBLICATIONS

Nagata et al., "Real-Time Analysis of Biomolecular Interactions," Chapter 1 & 2, Springer-Verlag Tokyo, 2000.

* cited by examiner

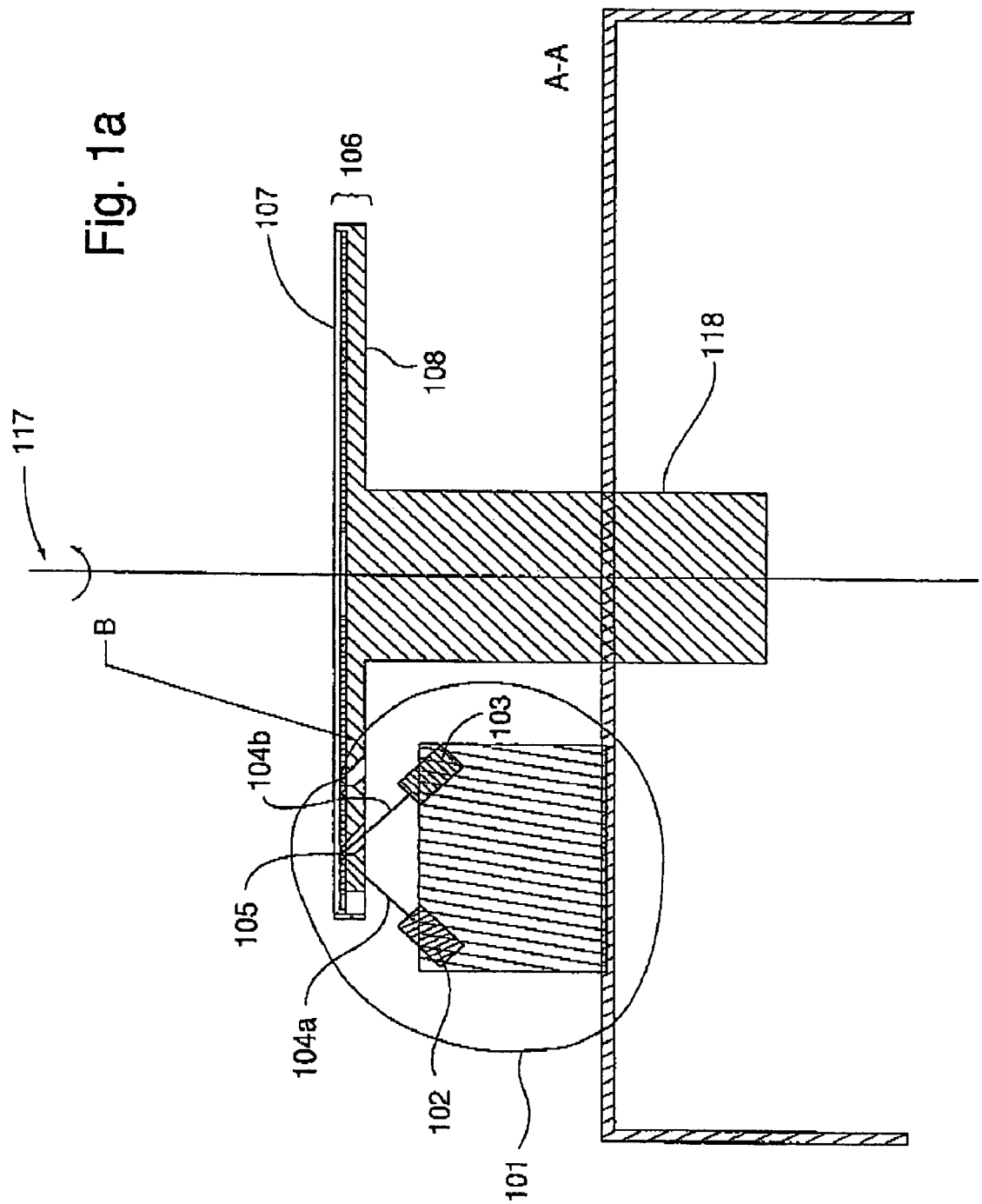

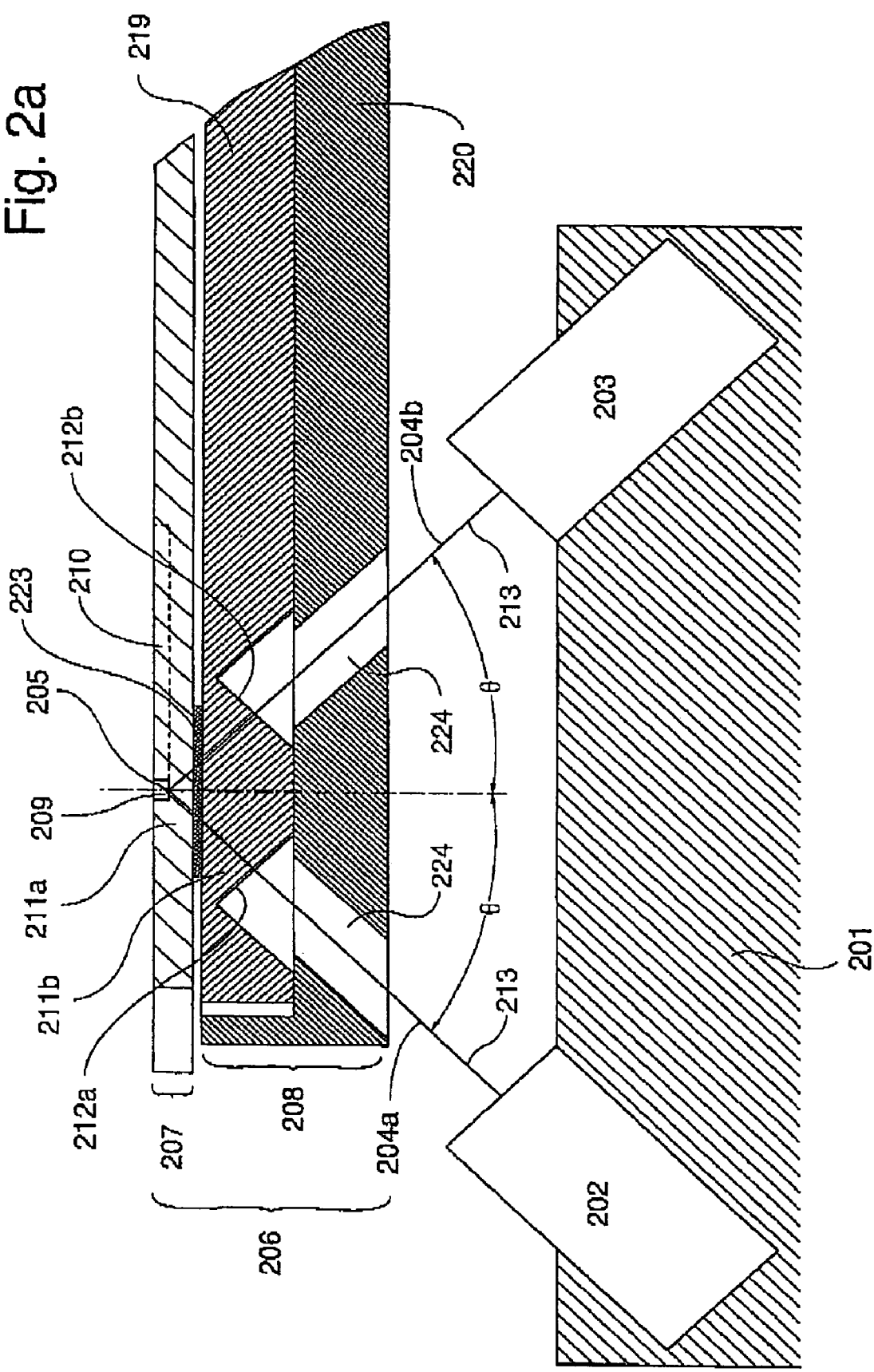

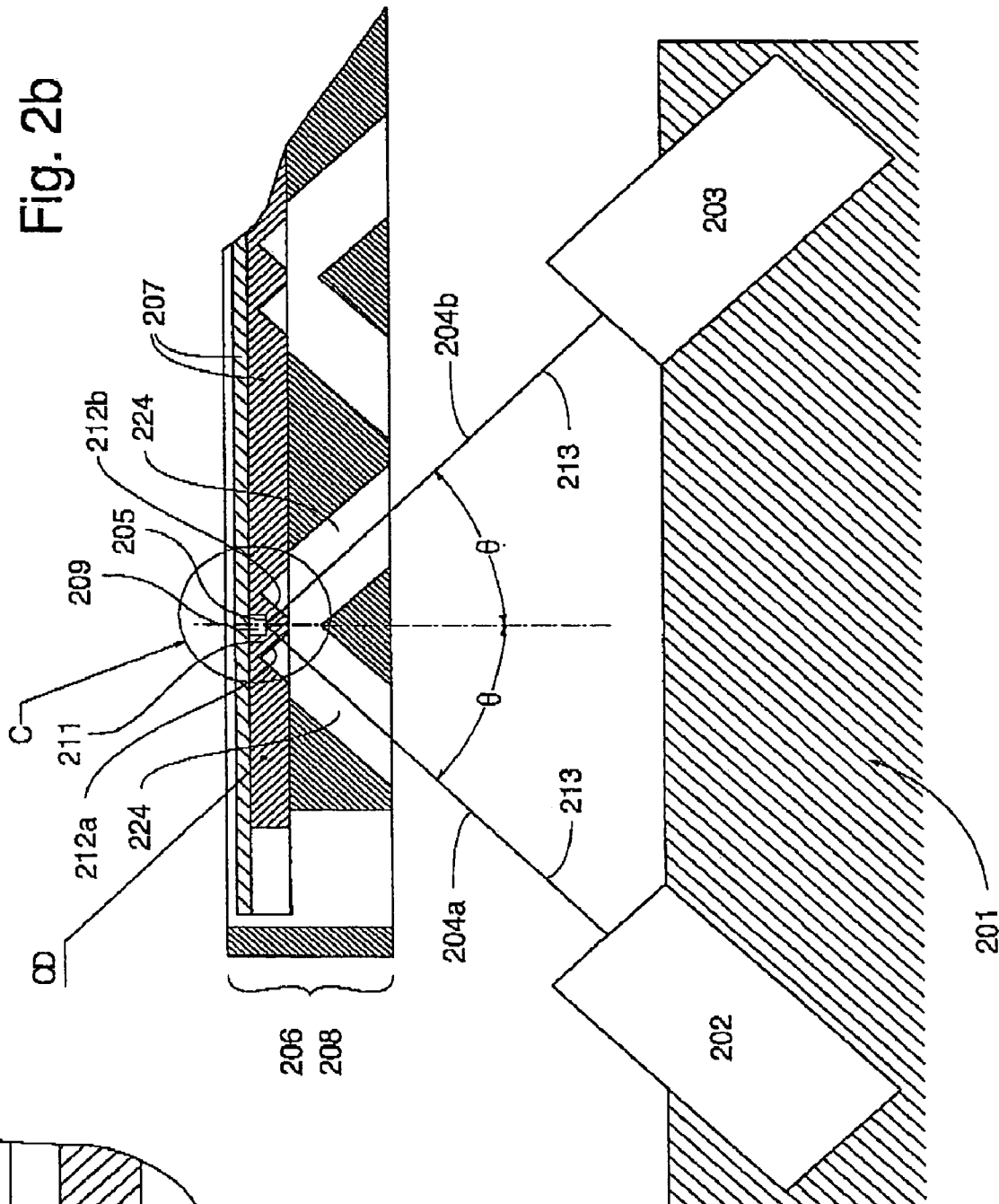
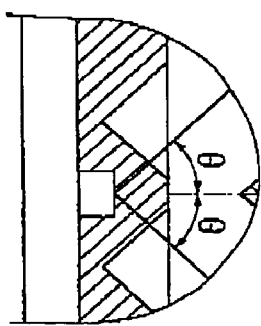

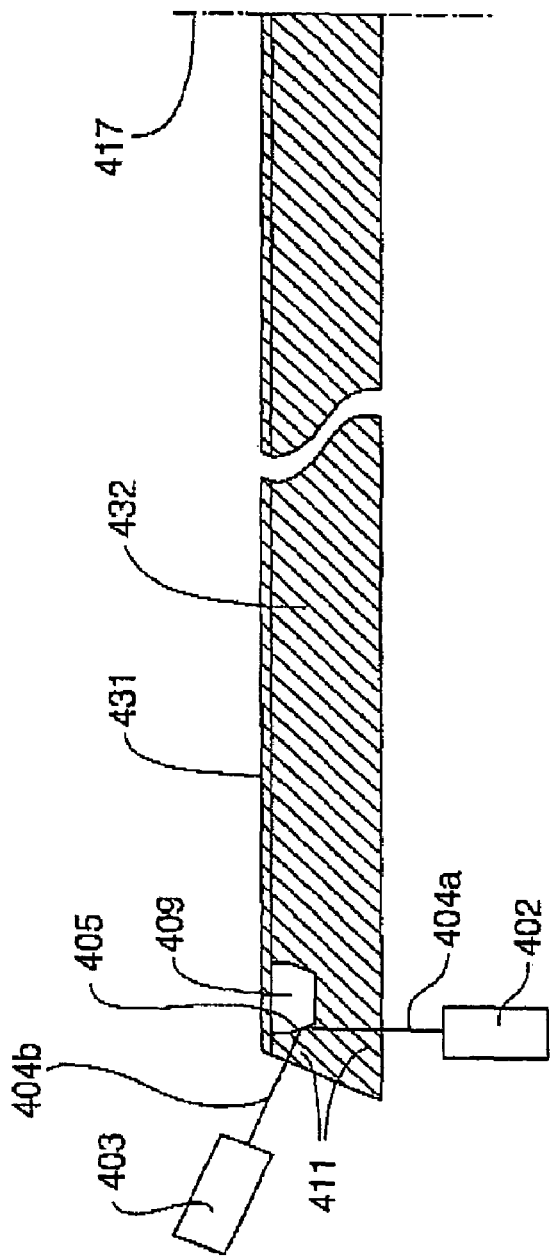
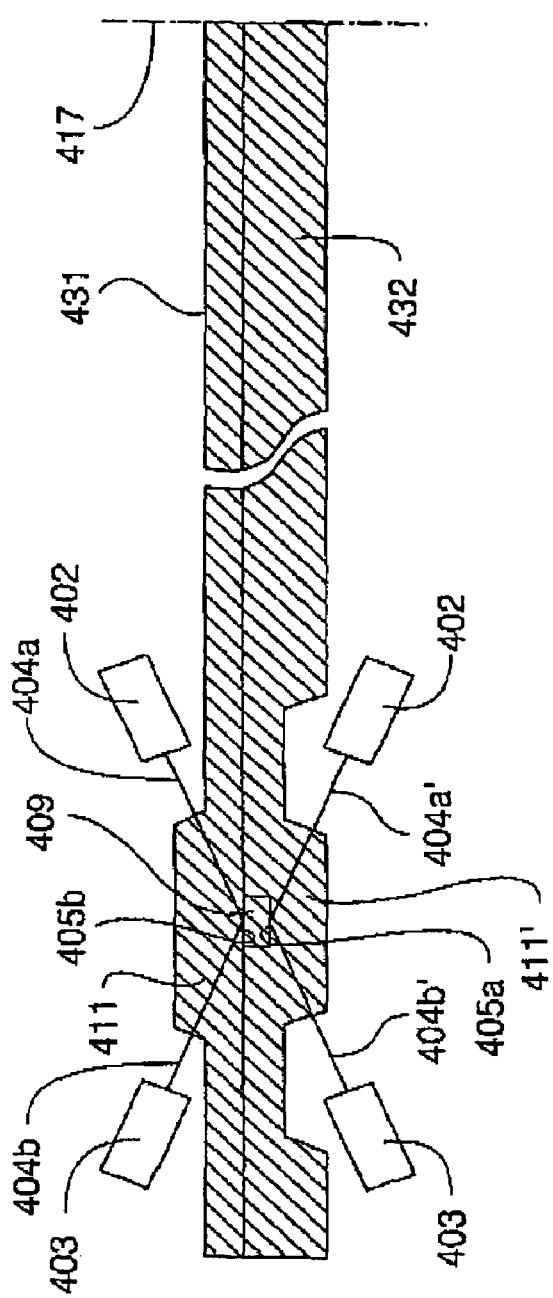
Fig. 4b
Fig. 4c

DETECTOR ARRANGEMENT BASED ON SURFACES PLASMON RESONANCE

CROSS-REFERENCE TO RELATED APPLICATIONS

This application is a continuation of International Application PCT/SE03/00876 filed May 28, 2003 and claims priority to U.S. Provisional Application No. 60/385,179 filed on May 31, 2002 and Swedish application No. 0201657.4, each of which is incorporated herein in its entirety.

TECHNICAL FIELD

The present invention concerns a detector arrangement, which comprises a detector unit, a rotatable microfluidic disc and means for appropriately scanning the surface of the disc in order to detect one or more substances that are present in detection microcavities (DMCs) that are present within the disc. The expression "to detect substances" includes detecting events taking place in one or more of the DMCs.

The DMCs are parts of microchannels structures that are present in the microfluidic disc. Liquid aliquots are transported and processed in the microchannel structures.

The detection principles utilized to detect substances in rotatable/spinnable microfluidic discs typically have been based on spectrometric methods. The principles mainly have been adapted for monitoring the results of the processing of liquids within microfluidic discs and for relating such results to one or more features of analytes. Typical features have been concentration, qualitative aspect such as affinity, structure, etc.

BACKGROUND OF THE INVENTION

In the context of the present invention SPR stands for Surface Plasmon Resonance as it is defined under the heading "SPR detector unit". See below. Undefined or other variants of SPR have been referred to in U.S. Pat. Nos. 6,338,820 and 5,994,150.

U.S. Pat. No. 5,994,150 (Imation Corp) describes an optical assaying system utilizing a rotatable disc with multiple sensing regions. The disc contains no detection microcavities or microchannel structures in which liquid flow is able to transport various reactants.

U.S. Pat. No. 6,338,820 (Alexion) describes an apparatus for performing a plurality of assays in a rotatable circular disc containing a plurality of concentrically arranged reaction sites. Certain variants of the disc may be microfluidic in the sense that the disc may have dispersion points for liquid that are connected via channels to the reaction sites. The assays contemplated are illustrated with chemical assays, biochemical reactions, cellular assays, physical assays, biophysical assays etc which then are further illustrated with e.g. surface plasmon resonance without specifying what is meant.

All patent applications and issued patents cited in this specification are incorporated by reference.

BRIEF SUMMARY OF THE INVENTION

During the last years we have come to the conclusion that it would be beneficial if one could monitor both a) reactions taking place within the individual microchannel structures, and b) presence or absence of liquid in microchannel structures of a microfluidic disc, for instance filling and emptying desired parts or functional units of a structure. We have also recognized that a detection principle that could be used for both alternatives would be of the greatest advantage because then the same detector unit might be used for monitoring events of type (a) and type (b). Thus one of the main objects is to design a detector arrangement comprising the same detection principle for measuring μM-concentrations of an analyte and the presence or absence of a liquid in a microchannel structure. The concentrations concerned are typically subintervals within the range $10^{-3}$-$10^{-12}$ M, for instance $\leq 10^{-6}$ M or $\leq 10^{-9}$ M. Still further objectives are to manage measuring even lower concentrations, such as down to $10^{-12}$ M or down to $10^{-15}$ M or down to $10^{-18}$ M or lower.

It would also be beneficial if a detector principle/arrangement meeting this demand only gives a signal when aligned with a detection microcavity. In this way it would be possible to minimize the need for a home mark on the disc, a separate home mark detector outside the disc and means for keeping track of which detection microcavity is aligned with the detector at a particular moment.

BRIEF DESCRIPTION OF THE DRAWINGS

FIGS. 1a-b give a schematic view of an arrangement according to the invention. FIG. 1a is a side view and FIG. 1b is a view from above.

FIGS. 2a-c illustrates two variants of discs/disc holders with different constructs of detection windows. In FIG. 2a a detection window is directed downwards and extends from the microfluidic disc into a separate plate of the disc holder. In FIG. 2b-c a detection window is fully integrated into the microfluidic disc.

FIGS. 4a-g illustrates schematically variants of microfluidic discs according to the invention. For reasons of simplicity only one out of many of the cells for measuring surface plasmon resonance (SPR-MCs) of a disc is shown. FIG. 4a shows a variant with the detection windows downwards. FIG. 4b shows a variant with a cell for measuring surface plasmon resonance (SPR-MC) which has detection windows both upward and downward combined with a SPR detection unit on each of the upward and downward sides of the disc. FIGS. 4c-g show variants in which the SPR surface is at an angle relative to the plane of the disc that is equal to the incident angle θ°. The light source (LS) and the light detecting subunit (LDS) are placed on opposite sides of the disc.

Figure 1B:
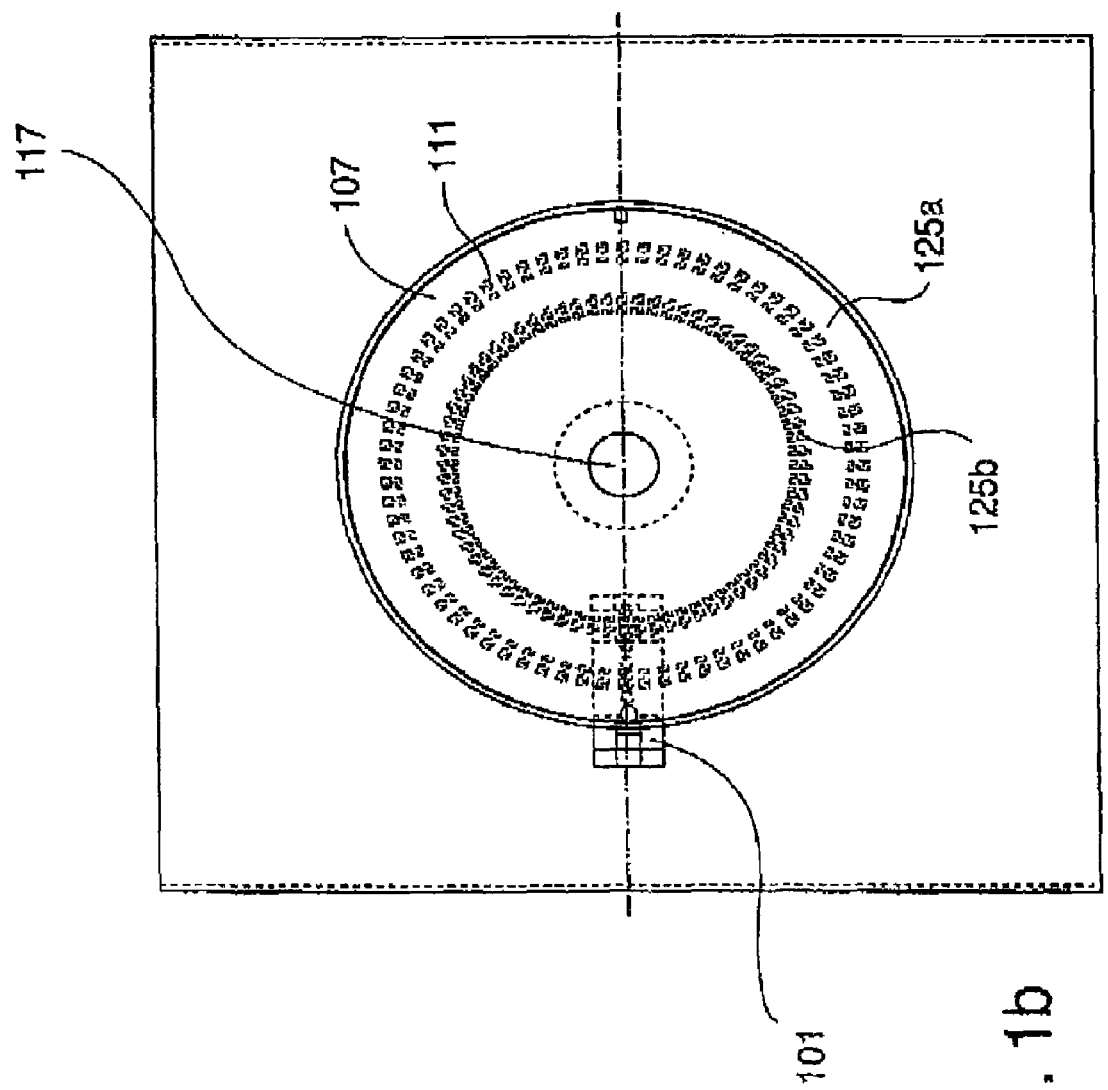

The first digit in the reference numerals relates to the figure number. Parts that have the same function in different figures have reference numerals in which the second and third digits are the same.

DETAILED DESCRIPTION OF THE INVENTION

We have recognized that the objects given above can be complied with if surface plasmon resonance (SPR) as defined herein is utilized as the detection principle.

In one aspect the present invention is the use of a surface plasmon resonance detector unit for detecting a substance that is present in DMCs of individual microchannel structures of a microfluidic disc. This also includes monitoring events taking place within the detection microcavities.

In another aspect, the present invention is a detector arrangement comprising a rotatable microfluidic disc and an SPR detection unit arranged such that the signal obtained from the SPR detector unit reflects a) the presence of a particular substance and/or
b) events taking place within detection microcavities (DMCs) of the individual microchannel structures of the microfluidic disc.

In a subaspect, the present invention is a detector arrangement (FIG. 1) that is characterized in comprising:

A. An SPR detector unit (101) that comprises an SPR illumination system (IS) (102), an SPR light detecting subunit (LDS) (103), and a beam path going from IS to LDS (104a and 104b). The beam path comprises an incident beam path (ibp) (104a) and a reflected beam path (rbp) (104b). The incident beam path (ibp) ends and the reflected beam path (rbp) starts at an SPR surface (105). The SPR surface and the parts of ibp and rbp that are next to the SPR surface is always a part of a rotary member (106) according to item (B) below.

B. A rotary member (106) that comprises one or more microfluidic discs (107) and a disc holder (108).

In the context of the present invention the incident angle θ° is the angle between the optical axis of the incident beam and the normal of the reflecting surface (in this case a surface plasmon resonance surface=SPR surface).

A. The SPR Detector Unit

The surface plasmon resonance (SPR) measuring technique is basically a differential refractive index detection. The opto-physical phenomenon is well known and means that total reflection from certain surfaces is attenuated for p-polarized light in terms of incident angle and wavelength, The surfaces are typically metallic and made for instance of gold, silver, aluminum etc and will henceforth be called SPR surfaces or SPR layers. The suitable thickness (X) of an SPR layer typically can be found within the interval <1000 nm, such as <500 nm. in the interval 10-1000 nm, and depends among others on the material in the layer. Preferred intervals are 10-1000 nm, such as 10-500 nm, 20-400 nm, and 10-500 nm. For gold the optimal interval typically is about 100 nm, i.e. found within the interval 100 nm±50 nm, such as 100 nm ±25 nm. The angle of reflection at which the attenuation occurs depends on angel of incident light (=incident angle), wave-length of the incident light, refractive index of the incident medium i.e. the medium closest to the SPR layer on the same side as the reflection is taking place, temperature, SPR surface/layer (e.g. type of metal and thickness), refractive index of the medium that is present closest to the SPR layer but on the side opposite to the incident medium etc. For further details see textbooks in the field.

Measuring cells utilizing SPR (SPR-MCs) are well known in the field. They have been used for monitoring molecular events at the surface of a microchannel containing a liquid. As illustrated in FIGS. 2a-c, an SPR measuring cell typically comprises a detection microcavity (DMC) (209) that is part of a microchannel structure (210), an SPR surface/layer (205) in one of the inner walls of the detection microcavity, and a detection window (DW) (211) that extends from the SPR surface/layer away from the detection microcavity. The detection window has one entrance surface (212a) for the incident light beam and one exit surface (212b) for the light beam (213) reflected in the SPR-surface (205). The medium to be analyzed is typically a liquid and is present in the detection microcavity (DMC).

By utilizing p-polarized light comprising a range of incident angles and keeping all other variables constant except for the medium in the detection microcavity, this kind of cells has been used for monitoring changes in refractive index that are taking place at the SPR surface within the detection microcavity. Typically, the side of the SPR layer in direct contact with the medium to be analyzed carries an immobilized affinity reactant and the medium contains a diffusible affinity counterpart to this affinity reactant. Upon formation of an affinity complex on the SPR surface, the refractive index of the medium next to the SPR surface will change which leads to a change in the angle at which attenuation of reflection occurs. From this change, possibly in combination with a standard curve or calibrator substances/values, it is possible to determine features of the diffusible affinity counterpart. An immobilized affinity reactant is not required, if the SPR measuring cell is to be used for measuring the presence or absence of a liquid.

Figure 3:
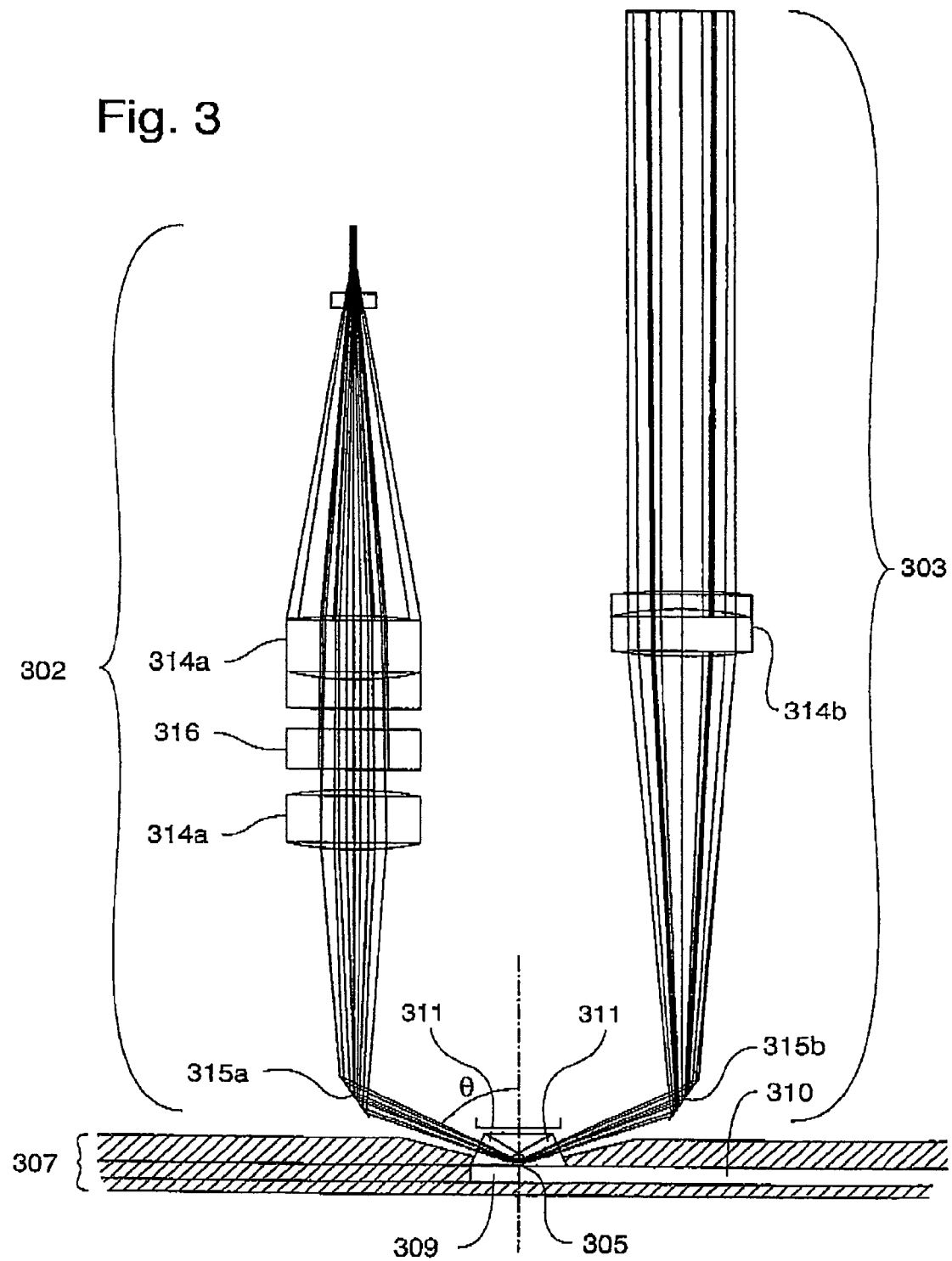
FIG. 3 illustrates the beam paths within the innovative arrangement.

The illumination system (IS) illustrated in FIG. 3 comprises the appropriate light source (LS) (302) with the appropriate beam path arrangement for focusing light on the SPR surface (305) via the detection window (311) (e.g. with a lens system (314a), and/or filters (316), and/or mirrors (315a) etc. In order to accomplish a sharp attenuation the illumination system should give mono-chromatic p-polarized light, typically selected with a wavelength within the interval of 1-1000 nm, such as 500-900 nm or 350-1000 nm, and with preference for 600-800 nm. The mean incident angle θ° is typically found in the interval of 45°-85°, in particular 55°-80°, such as 62°-72° (relative to the normal of the SPR surface). The light used may comprise a range of incident angles typically covering $\leq 10°$, such as $\leq 5°$ or $\leq 4°$, and $\geq 0.5°$, such as $\geq 1°$ or $\geq 2°$. The light beam reaching the SPR surface typically should be wedge-shaped or conical and comprise a mixture of incident angles within the ranges given. In alternative variants the range of incident angles is achieved by changing the incident angle during the measurement, for instance by moving the illumination system in relation to the SPR surface.

Monochromatic light in the context of the invention means light with a band-width in the interval 0-30 nm, such as 0-5 nm or 0-3 nm.

The light detecting subunit (LDS) (303) that also is illustrated in FIG. 3 is capable of determining at which angles the reflected beam is attenuated. Thus this subunit may comprise a photodetector array or any other suitable means (317) for detection of the reflected light, and the appropriate arrangement containing the necessary items for focusing the reflected light on the photodetector means (317) and placed at a position where it can collect and discriminate light of different reflection angles defined by the range of incident angles. Typically the necessary items include a lens system (314b) and possibly also a mirror (315b). Alternatively the photodetector part of the LDS only detects light of one reflection angle at a time but is movable relative to the SPR surface during the measurement so that it will collect light corresponding to the range of the angles of reflection.

The SPR principle has been outlined in a number of textbooks and review articles, including details about the illumination system, SPR measuring cells, and light detecting subunits, optics, incident angles, wavelengths etc. See for instance Nagata et al., "Real-Time Analysis of Biomolecular Interactions", "Part 2 General principles", Springer-Verlag, Tokyo, Japan (2000) pages 13-30. See also Patents Abstract of Japan, Volume 2000, No 2, Nov. 5, 2000 & JP 11 304693 A (Matsushita) and WO 0046589 (Vir A/S).

As illustrated in FIGS. 2a-c, the incident beam path (ibp) (204a) starts at the illumination system (202) and passes into a detection window (211) via an entrance surface (212a) of the detection window, and ends at the SPR surface (205).

The reflected beam path (rbp) (204a) starts at the SPR surface (205), leaves the detection window (211) via the exit surface (212b) of the detection window (211), and ends at the light detecting subunit (LDS) (203). Ibp and rbp (204a and 204b, respectively) never pass through the medium to be analyzed.

The SPR detector unit is typically non-rotatable about the axis of rotation of the rotary member. The unit may in preferred variants be laterally movable such that the intersection of ibp and rbp radially can transverse the surface of the rotary member in which the detection windows are exposed.

The plane defined by the incident beam path and the reflected beam path is typically orthogonal to the plane of the disc/rotary member. Relative to the radius of the disc/rotary member, the same plane may in principle have any direction, for instance parallel or orthogonal. It can be envisaged that increasing the angle between this plane and the radius would give more space for the SPR detection unit and therefore be more preferred. Accordingly, an essentially orthogonal arrangement, for instance within ±45°, such as within ±15°, are many times preferred. FIGS. 1-2 and 4a-e illustrate variants in which the beam path is parallel to the radius of the rotary member. In FIGS. 4f-g the arrangement is orthogonal.

B. The Rotary Member

This part will mainly be described with reference to FIGS. 1-2. The rotary member (106,206) has an axis of rotation (117) and comprises a disc holder (108,208) and one or more microfluidic discs (107,207). The disc holder typically is mounted on a spindle that is linked to a shaft of a rotor motor schematically shown as (118). The rotary member typically has an axis of symmetry ($C_n$) coinciding with the axis of rotation (117) and being perpendicular to the plane of the rotary member. n in $C_n$ is an integer 2, 3, 4, 5 or more with preference for n≧6, 7, 8 and ∞ ($C_\infty$=circular). The disc holder (208) may comprise a separate plate (219) between a plate holder (220) and the microfluidic disc (207) (see FIG. 2a).

The terms "radial distance" or "radial position" will henceforth refer to the shortest distance between an object and the axis of rotation.

The rotary member (106,206) is typically disc-shaped with three sides: the spindle side (221a), the side opposite to the spindle side (221b), and the edge side (221c). In the case there is a central hole for holding the disc in the disc holder there is also a forth side defining the hole. Since this side is occupied by retaining the disc in the disc holder this fourth side is not counted. The edge side is at the circumference of the disc-shaped rotary member. In a similar manner a microfluidic disc has three sides: the disc holder side (222a), the side opposite to the disc-holder side (222b) and the edge side (222c). The spindle side of the rotary member and the disc holder side of the disc will be called the lower side or the downward side. The opposite side will be called the upper side or the upward side. This terminology is irrespective of their orientation relative to the ground.

The rotary member comprises a number of SPR measuring cells (SPR-MCs) of the type defined above. The detection microcavity (DMC) and the SPR surface of an SPR-MC will typically always be part of the microfluidic disc. A detection window will have one part (P1) (211a) that is fully integrated into the microfluidic disc, and a possibly second part (P2) (211b) that is part of the disc holder (208). P1 extends from the SPR surface away from the detection microcavity (209,409) to the outer surface of the microfluidic disc. P2, if present, is in optical contact with P1, preferably via an opto-interface (223). See FIGS. 2a and 6.

The rotary member always contains a group of SPR-MCs (first plurality) that are at the same radial distance and with entrance surfaces and/or exit surfaces on the same side of the rotary member. This in most cases means that the parts P1 of the detection windows of these SPR-MCs end on the same side of the microfluidic disc, for instance in the upper or the lower side.

There may also be present another group of SPR-MCs (second plurality) that are oriented with entrance surfaces and/or exit surfaces to the same side as the first plurality but positioned at radial distances that are different from the radial distance of the SPR-MCs of the first plurality.

There may also be present a third group of SPR-MCs (third plurality) which is characterized in that their entrance surfaces and/or their exit surfaces are at a side of the rotary member that is different from the side carrying the corresponding surfaces of the first and second pluralities. The third plurality may comprise one subgroup of SPR-MCs that are located at the same radial distance and another group for which the SPR-MCs are located at other radial distances. The third group may have its entrance and/or exit surfaces at the lower or the upper side of the disc depending on which side is occupied by the corresponding surfaces of the first plurality of SPR-MCs.

The radial distances discussed for the SPR-MCs primarily refer to the radial distances of the entrance and/or exit surfaces of the detection windows.

The SPR-MCs including the SPR surfaces, detection windows, detection microcavities and the entrance and exit surfaces may be arranged as one, two or more concentric circles around the axis of rotation and/or in a spoke arrangement with the axis of rotation as the center. See FIG. 1b where there are two concentric circles (125a and b) of detection windows (111) on the lower side of the disc. The corresponding detection microcavities and microchannel structures are completely inside the disc and therefore not visible.

The detection microcavities may be arc-shaped or straight and essentially parallel to the periphery of the disc. Also other directions are possible, such as perpendicular to the periphery of the microfluidic disc (i.e. radial direction) and/or any other intermediary direction that might be defined by the individual microchannel structures of the microfluidic disc.

The optical axis of the incident and reflected beam paths are typically essentially orthogonal to the entrance and exit surfaces, respectively, of a detection window. This means that an entrance surface and an exit surface typically should be oriented relative to an SPR surface at angles that are essentially the same as the incident angle, i.e. +θ° and −θ°, respectively. See the figures.

The SPR surfaces are in many variants essentially parallel to the plane of the microfluidic disc, i.e. perpendicular to the axis of rotation.

In certain innovative arrangements there may be one, two or more SPR surfaces that are oriented relative to the plane of the disc at an angle that is >0° but <90°. In the case that the angle between the SPR surfaces and the plane of the disc may be equal to or close to equal to the incident angle θ°, either the incident beam path or the reflected beam path may be essentially parallel to the axis of rotation. This is illustrated fin FIGS. 4c-g in which the SPR surface (405) is in a sloped sidewall of the detection microcavity (409). One can envisage that this might a) simplify the way of configuring the illumination system and the light detecting subunit in the arrangement (as illustrated in FIGS. 4c-g), and/or b) reduce the demand on planarity and the negative effect wobbling might have in the case measurement is done while spinning the rotary member.

By rotating the rotary member around the axis of rotation, it will be possible to replace the parts of ibp and rbp that are within a particular SPR-MC with the corresponding parts of any other of the remaining SPR-MCs that are within the same radial distance. By laterally moving the SPR detector unit and/or the rotary member, it will be possible to replace the parts of ibp and rbp of SPR-MCs that are at different radial distances but at the same angular position with each other. By combining rotation and lateral movement, the SPR-MCs can replace each other independent on their radial or angular position. These general rules apply provided all the detection windows are oriented in the same way relative to the plane of the microfluidic disc.

B.1. The Microfluidic Disc

Typically there is only one disc associated with a disc holder in the rotary member but as described below there may be also two, three or more.

A microfluidic disc that is to be used alone in the rotary member typically has an axis of symmetry ($C_n$) that is perpendicular to the plane of the disc. When the disc is placed in the disc holder this axis of symmetry coincides with the axis of rotation of the rotary member. n in $C_n$ is an integer 2, 3, 4, 5 or more, with preference for n≧6, 7, 8 . . . ∞ ($C_\infty$). The circular disc form ($C_\infty$) is preferred.

In variants where two or more discs are used simultaneously in the same disc holder they are typically placed without overlap therein. Discs that are to be used simultaneously should have the same geometric form and be placed symmetrically around the axis of rotation. Examples of geometric forms are: sector-like, rectangular, oval etc.

A microfluidic disc comprises a plurality of essentially equal microchannel structures that are enclosed within the disc. In each of the microchannel structures one or more reactants are to be transported between two, three or more functional units by a liquid flow. The liquid flow in turn is, according to the invention, typically driven by inertia force, for instance centrifugal force, and/or capillary force. Other forces may alternatively be used or combined with these kinds of forces. The term "reactant" includes analyte. The reactants and/or the liquid aliquots as such are typically processed in a microchannel structure, and the result of the processing is determined in a detection microcavity (DMC) that typically is positioned in a downstream part of the microchannel structure, i.e. downstream an inlet port. Typical functional units in addition to DMCs are volume defining units, transport channels, units for separating particulate matters, units for separation based on affinity for a ligand that is attached to a solid phase, mixing units, units for performing chemical reactions such as enzyme reactions, affinity reactions etc, valves etc. Each microchannel structure starts at an inlet port for liquid, passes one or more functional units of the types given above and ends in an outlet port that may be for liquids and/or air (outlet air vent). There may be additional inlet ports and outlet ports. Such ports may be for liquids and/or air (inlet and outlet vents, respectively). An inlet port or an outlet port may be common for two, three or more microchannel structures. The presence of a plurality of microchannel structures enables timely parallel transport and processing of liquid aliquots and reactants that have been dispensed to inlet ports.

Each microchannel structure may comprise one, two or more detection microcavities (DMCs) of the kind defined above.

The ports may be located to the same side or to different sides of the microfluidic disc. Typically inlet ports for liquids are located to the upper side of the disc. In the case that ports are located to the lower side of the microfluidic disc it becomes important to secure that the disc holder provide unhindered access, for instance to ambient atmosphere, around these kinds of openings for their proper functioning.

In order to use centrifugal force for driving a liquid flow within a microfluidic disc, the disc should be a) spinnable around the axis of rotation, and b) each microchannel structure should have an upstream part that is at a shorter radial distance from the axis of rotation than a downstream part, when placed in the disc holder of the present innovative arrangement. This in many cases means that each microchannel structure has an inlet port at a shorter radial distance than one of the functional units, e.g. an outlet port or a detection microcavity. The outlet port may be an outlet for liquid.

Centrifugally based microfluidic discs with microchannel structures and measurement cells to be used for detection principles other than SPR have been disclosed in a number of scientific articles and patent publications. The microfluidic principles then outlined could typically be used also in the present invention except that the cells for measurement have to be adapted to surface plasmon resonance. Centrifugally based microfluidic platforms have been described in WO 03025548 (Gyros AB), WO 02075312 (Gyros AB), WO 02075775 (Gyros AB), and WO 02075776 (Gyros AB), WO 9721090 (Gamera Bioscience), WO 9807019 (Gamera Bioscience) WO 9853311 (Gamera Bioscience), WO 9955827 (Gyros AB), WO 0040750 (Gyros AB), WO 0147638 (Gyros AB), WO 0146465 (Gyros AB), U.S. Pat. No. 5,160,702 (Molecular Devices Corp,), U.S. Pat. No. 5,472,603 (Abaxis) etc.

The term "plurality" in the context of the invention contemplates two, three or more of an item (e.g. microchannel structures, SPR-MCs etc). Thus plurality may mean ≧10 or ≧25 or ≧50 or ≧100 or ≧200 essentially equal items, e.g. microchannel structures. For microchannel structures the term "plurality" typically contemplates 96, 384, 1536, etc structures, possibly plus ≦10% of excess structures in order to secure that one microchannel structure per well of a microtitre plate is available. Excess structures are also called redundant structures and may be present also in larger numbers. See for instance WO 030872730 (Gyros AB) and corresponding U S application 20030211012.

The terms "microchannel", "microconduit", "microformat" etc contemplate that a) a microchannel channel structure comprises one or more cavities and/or channels/conduits that have a cross-sectional dimension that is ≦$10^3$ μm, preferably ≦$10^2$ μm, and/or b) the volumes of the microcavities/microchambers and/or the liquid aliquots to be processed are in the μl-range, i.e. ≦1000 μl such as ≦100 μl or ≦50 μl including the nl-range (nanoformat), such as ≦5000 nl or ≦1000 nl or ≦500 nl or ≦100 nl or ≦50 nl.

The microfluidic disc is typically manufactured from two planar substrates, at least one of which is microstructured in one of its sides in such a manner that the microchannel structures of the final microfluidic disc are formed when joining the microstructured side of one substrate with a possibly microstructured side of the other substrate. Either one or both of the substrates may have through-going holes that are associated with individual microchannel structures in the final microfluidic disc. These holes may be used as ports, i.e. inlets or outlets for liquids and/or as inlet or outlet vents for air.

Inorganic and/or organic material constitute an essential part of the substrate. Typical inorganic materials are silicon, quartz, glass etc. Typical organic materials are polymer materials, for instance plastics including elastomers, such as rubber silicone polymers (for instance poly dimethyl siloxane) etc. Suitable polymer materials and plastics typically comprise polymers that are obtained by addition polymerization, condensation polymerisation, polymerisation of unsaturated organic compounds etc. The microstructures may be created by various techniques such as etching, laser ablation, lithography, replication by embossing, moulding, casting etc, etc.

Substrates that expose surfaces and microstructures in plastics are many times preferred because the costs for plastics are normally low and mass production can easily be done. See for instance WO 9116966 (Pharmacia Biotech AB, Öhman & Ekström). By using plastics for the manufacture the microfluidic discs may become disposables. At the priority date of the present invention, the preferred plastics were transparent with a refractive index typically within the interval of 1.45-1.55. Typical examples are plastics that comprises polyolefins obtained by polymerization of monomeric olefins in which there is a straight, branched, and/or cyclic aromatic or non-aromatic structure, e.g. Zeonex™ and Zeonor™ from Nippon Zeon, Japan. This does not outrule the use of other transparent plastics having acceptable refractive index and potentially comprising polycarbonates, polystyrenes, polymethacrylates and/or the like. This selection criterion based on refractive index in particular applies to substrates that contain the parts P1 of the detection windows.

The entrance and/or the exit surfaces with the appropriate angles relative to the plane of the disc may be introduced in the form of prism surfaces by replication against a surface carrying the inverse microstructure. Alternatively, one can envisage that prisms with the appropriate surfaces may be separately attached either before or after the substrates have been joined together.

There are a number of techniques for joining the two substrates together. See for instance WO 9424900 (Ove Öhman), WO 9845693 (Soane et al), U.S. Pat. No. 6,176, 962 (Soane et al), WO 9956954 (Quine), WO 0154810 (Derand et al), WO 9832535 (Lindberg et al), WO 0197974 (Chazan et al), and WO 03055790 (Gyros AB) and corresponding U S application 20030129360.

Before joining the two substrates together the SPR surface/layer is locally introduced at detection window positions of surface parts that are to become inner walls in the final device, i.e. in an uncovered microstructure and/or in a flat part of the surface of the opposite substrate.

The microfluidic disc described above in which centrifugal force can be used for creating a liquid flow in each of one, two or more of the microchannel structures constitute a subaspect of the invention. The flow is capable of transporting reactants from an upstream functional part to a downstream functional part. Accordingly the present invention provides a microfluidic disc (107,207,307,407, 107) having an axis of symmetry (117,417) as discussed above and comprising a plurality of microchannel structures, each of which has an upstream functional part that at least partly is at a shorter radial position than a downstream functional part and in fluid communication with said downstream functional part. This disc is characterized in that there are detection microcavities (DMCs) (209,309,409) in at least a part of said microchannel structures and that each of said DMCs has an SPR surface (205,305,405) on an inner wall. The inner wall (detection window) (211,311,411) extending from the SPR surface to the surface of the disc is in a material that is translucent for light normally contemplated for surface plasmon resonance. Materials and designs of SPR surfaces and inner walls between the SPR surface and the surface of the disc are as discussed elsewhere in this text.

This subaspect also comprises that the microfluidic disc is combined with a disc holder plate (219) comprising the remaining parts P2 (211b) of the detection windows (211) if they are incomplete in the microfluidic disc. This subaspect also comprises that an opto-interface plate is combined with the microfluidic disc and the disc holder plate (219). For disc holder plate and opto-interface plate see elsewhere in this specification.

Figure 4A:
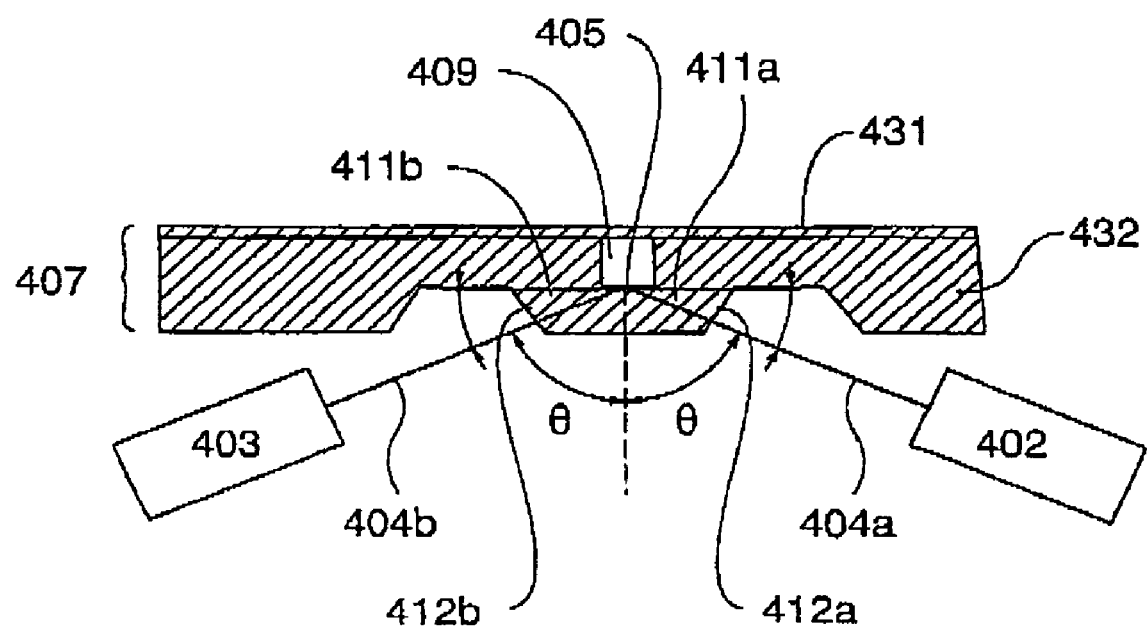
Figure 4D:
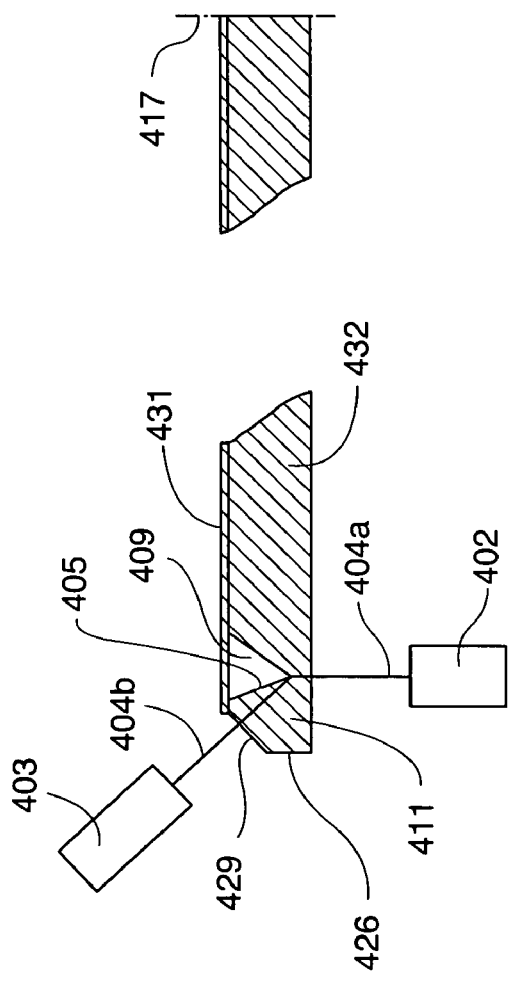
Figure 4E:
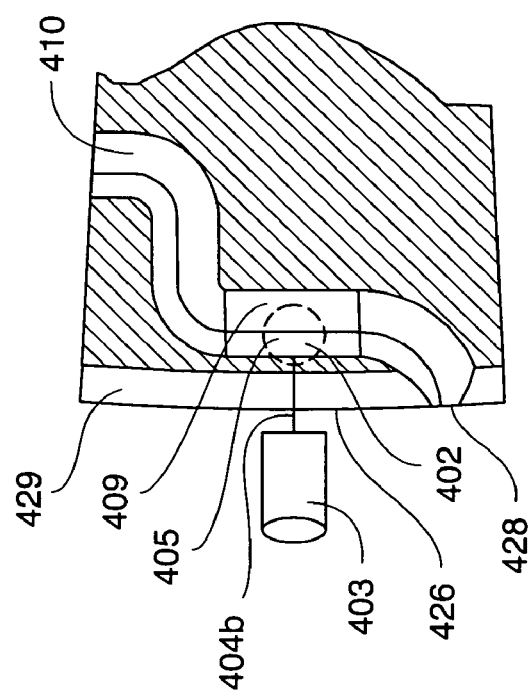
Figure 4F:
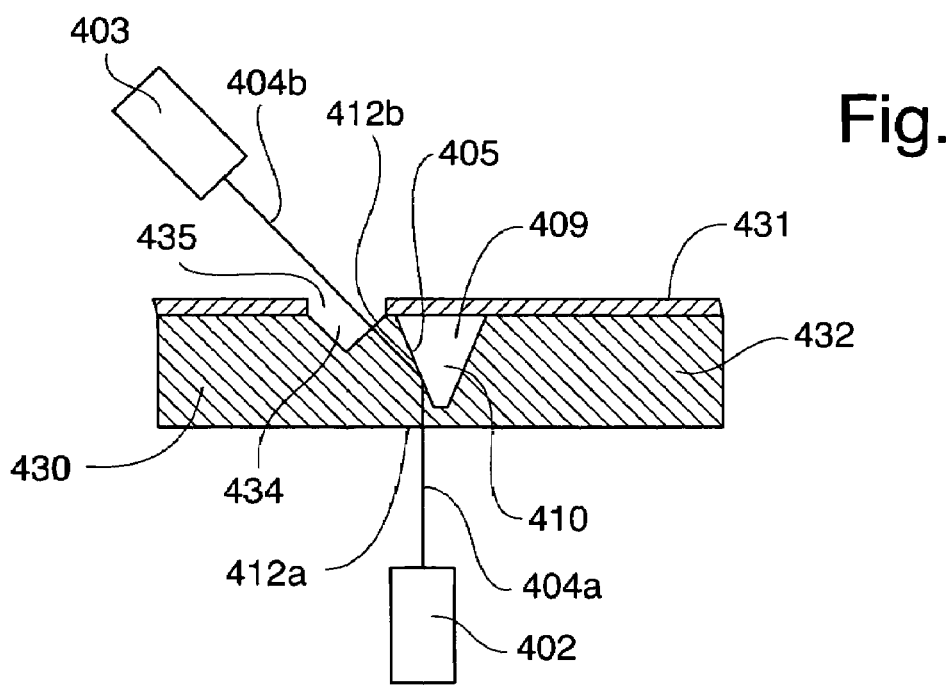
Figure 4G:
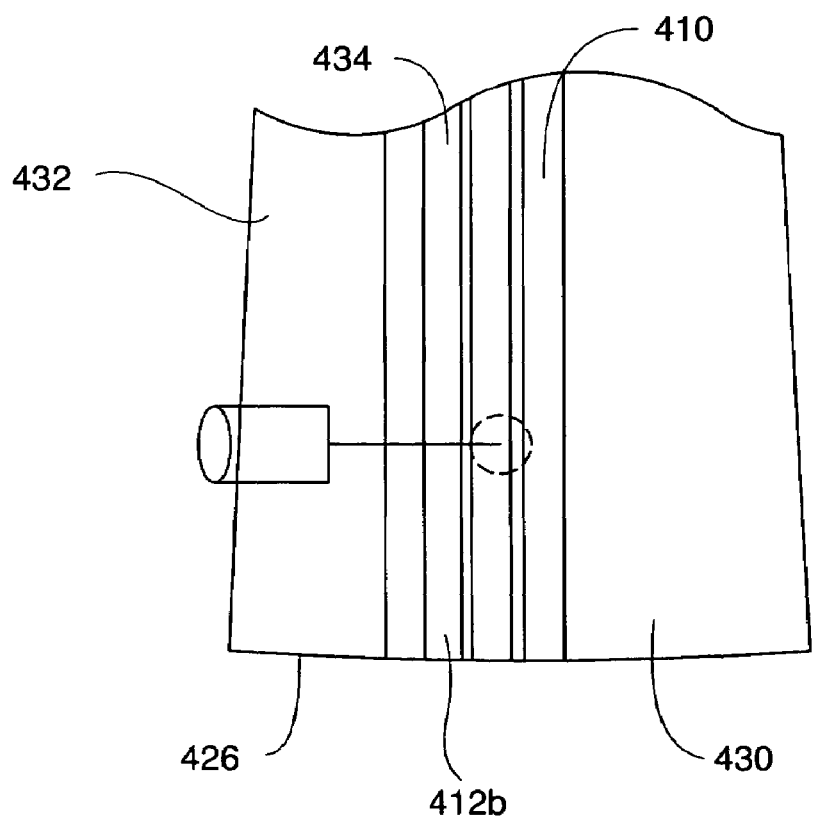

FIGS. 4a-g illustrate three variants of microfluidic discs in which the complete detection window (411) including the SPR surface (405) and the entrance surface (412a) and the exit surface (412b) are part of the disc. The figures have been simplified showing only one of the SPR-MCs/microchannel structures in enlarged form. The axis of symmetry (axis of rotation) has been indicated (417) in some of the figures. The light source (402) with incident beam path (404a) and light detecting subunit (403) with reflected beam bath (404b) are in principle interchangeable. The plane defined by the incident beam (404a) and the reflected beam (404b) is for the variants of FIGS. 4a-e aligned radially and for the variants of FIGS. 4f-g orthogonal to the radius of the microfluid disc. The portions of the microchannel structure that are upstream and downstream the detection microcavity (409) in FIGS. 4a-c are not visible because these portions are not at the same angular position as the detection microcavity. The detection microcavity (409) is essentially parallel to the circumference of the disc.

FIGS. 4a-b illustrate variants in which the SPR-surface is essentially parallel to the plane of the disc and the entrance surface (412a) and the exit surface (412b) essentially at the angles $-\theta°$ and $+\theta°$ relative to the disc plane (i.e. the same as incident angle/reflecting angle).

FIGS. 4c-g illustrate variants in which a) the SPR surface is essentially at the angle $\theta°$ relative to the plane of the disc, b) the entrance surface (412a) essentially parallel to the disc plane and c) the exit surface (412a) essentially at the angle $\theta°$. The incident beam is orthogonal to the plane of the disc.

FIGS. 4d-e illustrate a variant of a disc in which there is a peripheral detection microcavity (409) which is essentially parallel to the circumference of the disc. FIG. 4d is a cross-sectional view of the disc along a plane which is perpendicular to the plane of the disc and passes through the center (axis of rotation) (417), a detection microcavity (409) and the edge (426) of the disc. FIG. 4e is a view seen from above of an outer part of a sector of the disc surrounding said plane. The cross-sectional area (427) of the detection microcavity (409) is triangular. The detection microcavity (409) is part of a microchannel (410) that in the downstream direction is ending in an outlet (428) placed in the circumferential edge (426) of the disc. The SPR surface (405) is angled relative to the plane of the disc such that the incident beam (404a) is orthogonal to the plane of the disc. The upper part of the circumferential edge (429) is sloped at least at the position of the surface of the detection window (411) such that the reflected beam (404b) will leave through the exit surface (412b) orthogonally. The light source (402) and the light detecting subunit (403) are placed on different sides of the disc.

FIGS. 4f-g illustrate a variant with an elongated detection microcavity (409) that is aligned radially and part of a microchannel (410) that ends in the circumferential edge (426) of the microfluidic disc (407). The microchannel part shown coincides with the detection microcavity. FIG. 4f is an edge-view of a sector (430) of the disc. FIG. 4g shows the same sector (430) seen from above with the upper substrate (431) removed and the lower substrate exposed (432). The cross-sectional area of the detection microcavity (409) and the configuration of the SPR detector are similar to the variant illustrated in FIGS. 4d-e. Since the exit surface (412b) in this variant is not placed in the edge of the circumference, there is a separate groove (434) in the lower substrate (432). This groove (434) is parallel to the detection microcavity (409) and provides the exit surface (412b) angled appropriately relative to the reflected beam path (404b). The upper substrate (431) then comprises a corresponding through-passing opening (435) that also is elongated and parallel to the detection microcavity (409). The light source (402) and the light detecting subunit (403) are placed on different sides of the disc. The configuration leaves good space for radial movement of SPR detector unit.

B.2. The Disc Holder

The disc holder will be described in reference to FIGS. 1, and 2a-c. The disc holder (108,208) is part of the rotary member (106) and is attached to a spindle, which in turn is connected to a shaft of a motor schematically shown as (118). The motor is capable of rotating the shaft, spindle and rotary member around a common axis of rotation (117). The disc holder has an axis of symmetry as discussed above for the rotary member and provides essentially planar support for a microfluidic disc (107,207)) that is seated on the rotary member (106,206). This includes that the rotary member is disc-shaped, comprises spokes extending radially outwards from the axis of rotation etc. If the rotary member provides a disc-shaped surface to support the microfluidic disc it may contain openings passing through the disc. These kinds of openings may be used for the beam path to reach detection windows that are located in the lower side of a microfluidic disc, and for providing subpressure to retain the disc in the disc holder, for instance.

In order for the detector arrangement to work properly it is important that the disc holder defines a support plane of sufficient planarity for the microfluidic disc(s). This in particular applies if the disc(s) is/are made in plastics and easily are skewed. The support plane is primarily defined by the local areas in the disc holder that are to be contacted with local areas in the lower surface of the microfluidic disc. Typically the most important local areas of the disc in this context is in close association with the parts P1 of the microfluidic disc. This demand for planarity becomes particularly stringent when high sensitivity is required, e.g. when determining features of an analyte that is present in the concentration ranges outlined under the heading "Objects of the Invention". Accordingly, the support plane typically has a planarity, which is dependent on use and has been selected in the interval 0-100 µm. When looking for increased sensitivities the selection has to be made in more narrow subintervals, such as $\leq 50$ µm or $\leq 25$ µm or $\leq 10$ µm or $\leq 5$ µm or $\leq 2$ µm. The support plane is typically defined by a disc-shaped plate fabricated in glass, steel or any other rigid material that is able to provide surfaces of a high degree of planarity. Spoke arrangements and other arrangement in forms that is capable of defining support planes of sufficient planarity (discontinuous contact area) may also be used.

There exist a number of different ways for firmly holding the microfluidic disc on the disc holder. One alternative means that the disc holder has holding means for the center and/or the periphery of the microfluidic disc. In preferred variants and in particular if characterization of analytes in microfluidic discs made in plastics is concerned, it can be envisaged that an evenly applied subpressure through the disc holder against the microfluidic disc will promote planarity. To accomplish this a vacuum source may be connected to a non-rotatable part of the arrangement for providing sub-pressure to a) openings, b) a system of microchannels etc that are present in the support surface of the disc holder. A system of microchannels in this context also comprises an evenly roughened form of the support surface, e.g. blasted. These openings and channel systems may be evenly distributed across the top surface of the disc holder, but it is often more important to secure equal subpressure adherence to the lower surfaces of the disc close to or at the positions of the SPR-MCs. Utilizing sub-pressure in the context of rotatable substrates in microfluidic discs has been described in WO 03025449 (Gyros AB) and U S 20030082075.

The disc holder may be designed as a cassette in which two or more discs are place more or less side by side. In this variant there may be separate positioning means for each disc. Thus the rotary member may provide fixation means that fit to the form of each individual disc. If the rotary member provides a more or less continuous support surface the fixation means may be in the form of a depression matching exactly the disc. There may also be adjustable means such as pins, clamps or the like permitting different forms of discs to be seated in the disc holder. It is important that the discs are placed symmetrically on the disc holder in order not to imbalance the rotary member if higher spinning speeds are to be used for creating liquid flow within the disc or for measuring with the SPR detector unit while spinning, for instance. Subpressure may also be used.

The entrance and exit for radiation to/from may be on any side of the microfluidic disc (107,207), i.e. the upper, lower and/or edge side. Typically, however, entrance and exit are via the lower or the upper side, i.e. on the opposite or on the same side as the disc holder. In the latter variants it is important that the disc holder does not hinder passage of light in ibp and rbp. Therefore the disc holder may provide channels and/or other free spaces (124, 224) going from the entrance and exit surfaces (212a and 212b, respectively) to the lower surface of the disc holder. Alternatively, the detection windows may extend downward through the disc holder without need for this kind of channels.

As discussed above the disc holder (108,208) may comprise a part P2 (211b) of the detection windows (211) provided the detection windows and the disc holder are on the same side of the microfluidic disc. An illustrative example is that the disc holder comprises a separate plate (219) (disc holder plate) of sufficiently high planarity and have a size providing support for the disc(s) that is/are placed in the holder (as discussed above). In addition to the disc holder plate, the disc holder then also comprises a plate support holder (220), which provides for the channels and the empty space (124,224) through which ipb and rpb are passing. The disc holder plate (219) typically is made of a material that a) has essentially the same optical properties (refractive index) as the detection windows for the light from the light source, and b) carries on its lower side the entrance and exit surfaces that match the parts P1 of the detection windows of the microfluidic disc.

The entrance and exit surfaces may be in the form of the prism surfaces.

In order for light to pass across the interface between P1 (211a, FIG. 2a) and P2 (211b, FIG. 2a), an opto-interface (223, FIG. 2a) is placed between P1 and P2 for each of the detection windows that comprise both P1 and P2. The techniques for creating appropriate opto-interfaces for SPR measurements are well known in the field. See for instance U.S. Pat. No. 5,164,589 (Biacore AB) and WO 9719375 (Biacore AB). Typical materials for opto-interfaces are in the form of oils (immersion oils), or more preferably in form of optical transparent elastic material (opto-interface gel) that should have essentially the same refractive index as the material in P2 and P1. Suitable material may be selected amongst transparent rubbers or elastomers that may be cross-linked to various degrees, and transparent epoxy resins. Useful materials are commercially available.

In a preferred variant (FIG. 5) the opto-interface material is part of plate (536) (opto-interface plate), which is placed between the top surface of the disc holder (508) and the microfluidic disc (507). At the position of each detection window (511) this plate exposes an opto-interface material (523a,b) to both P1 and P2 when the opto-interface plate (536) is properly aligned in the disc holder. In other words the plate exposes an opto-interface material on both sides of the opto-interface plate at least at the positions that are to be aligned with P1 and P2 of a detection window.

The opto-interface plate may comprise a continuous support plate (537, opto-interface support plate) of translucent material of essentially the same refractive index as P1 and P2. The opto-interface material (538), preferably an opto-interface gel, is then placed on the upper and lower sides of the opto-interface support plate (537) and covers at least the positions of the detection windows.

Figure 5:
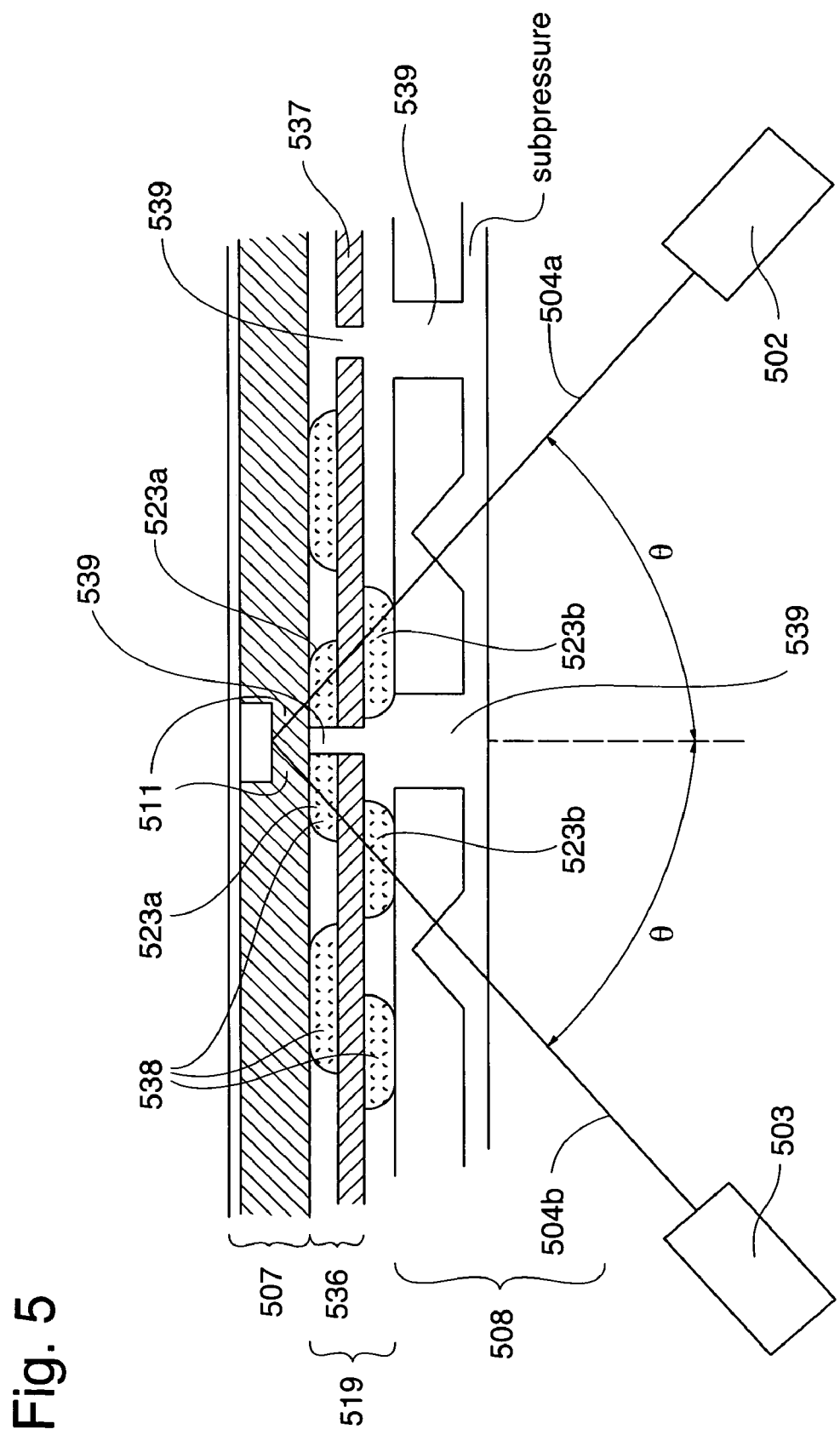
FIG. 5 illustrates a variant of accomplishing optical contact between the disc holder and the microfluidic disc by the use of a so-called opto-interface plate.

In one variant the opto-interface material is localized to parts of each of the upper and lower sides of a continuous opto-interface support plate (537) (FIG. 5). The pattern of the opto-interface material is such that it will provide optical contact for P1 and P2 in each detection window. Each piece of opto-interface material may cover one two, three or more detection windows and is typically thicker in the center of each piece, for instance dome-shaped or stepped as suggested in U.S. Pat. No. 5,164,589 (Biacore AB) and WO 9719375 (Biacore AB). The material may be in form of ridges that may cover arc-shaped, rectangular-shaped etc subareas on the upper and/or lower side of the opto-interface plate (537). The material may be arranged as one two or more continuous or discontinuous annular concentric rings around the center (axis of rotation) of the disc.

In another variant the opto-interface material forms a continuous layer on either one or both of the sides of an opto-interface support plate (537), possibly with raised parts at the detection windows in analogy with what has been discussed for the first variant.

In still another variant the opto-interface support plate (537) have through-passing holes in which the opto-interface material, typically in the form of an elastic material is placed.

In still another variant the opto-interface plate is moulded in an opto-interface material.

The opto-interface plate (536) is placed in the disc holder with the opto-interface material matching the parts of the detection windows in the microfluidic disc (507) and the plate (519) (parts P1 (511a) and P2 (511b), respectively).

When pressed together the shape and elasticity of the opto-interface material will assist in avoiding inclusion bubbles of air that may adversely affect the optical properties of the opto-interface.

Further information on the selection and shape of the opto-interface material is found in U.S. Pat. No. 5,164,589 (Biacore AB), WO 9719375 (Biacore AB) and other publications in the field.

In case subpressure is used for retaining the microfluidic disc in combination with an opto-interface plate, there should be channels (539, subpressure channels) or openings providing subpressure from the disc holder.

It is beneficial that the various parts of the rotary member such as the disc holder/plate holder, opto-interface plate, plate carrying P2 parts of detection windows, microfluidic disc(s) etc comprises guiding means that facilitates proper alignment of the parts P1, parts P2 and channels and open spaces in the disc holder both before, after or during rotation/spinning of the rotary member. Guiding means may be physical, for instance in forms of matching indentations, pins, holes etc, or adaptive and controlled by software. The latter may be illustrated by automatically adjusting the alignment between the microfluidic disc and the parts of the beam paths in the disc holder as a function of the signal obtained by an SPR detector unit before the different parts are firmly clamped to each other, for instance by applying subpressure.

Other Parts of the Detector Arrangement

As discussed above the innovative arrangement comprises a motor (rotor motor) that is capable of rotating the rotary member for position SPR-MCs of the same radial distance (first plurality) in front of the intersection between ibp and rpb. The motor should permit stepwise rotation enabling measurement in an SPR-MC each time ibp and rbp are complete and the incident beam targets an SPR surface. One can also envisage measurement during continuous spinning, possibly combined with intermittent measurement each time the incident beam is able to target an SPR surface.

The rotor motor preferably should permit a wide range of rotation speeds, for instance from 0 up to 15 000 or 20 000 or 30 000 rpm or even faster. The motor should permit stepwise rotation and/or continuous spinning or rotation, and optionally be regulatable. This will enhance the versatility of the innovative arrangement since a) spinning may be used to create sufficient centrifugal force for driving liquid flow in parallel within the individual microchannel structures of the disc(s) and b) measurement of the various SPR-MCs can be performed.

Spinning for driving liquid flow and rotating/spinning for measurement may be done with the same rotor motor or with different rotor motors. If different motors are used the microfluidic disc is typically transferred to the appropriate motor arrangement before the particular operation is performed.

As discussed above the rotary member may also contain SPR-MCs (second plurality) that are at radial distances that are different from those of the first plurality. In these variants the rotary member and/or the SPR detection unit is/are linked to a translational responder for incremental changing the radial position of the SPR detector unit (in fact the intersection between rbp and ibp) thus enabling measurement in the SPR-MCs of the second plurality.

In the case both the first and the second plurality of SPR-MCs are present in the rotary member the two motors may be coordinated so that measurements are carried out in all or in a predetermined subgroup of the SPR-MCs. The possibility of measuring will become independent of radial and angular positions of the SPR-MCs.

The measurement is typically under control of a controller comprising the appropriate software and hardware.

The control of the alignment of the SPR detector unit with the SPR-MCs and/or measurement are following general principles known in the field for other detection principles. Particularly advantageous methodologies are disclosed in WO 0325548 (Gyros AB) and U S 20030054563 (GYROS AB) and WO 03087779 (Gyros AB) and corresponding U S application 20030231312. In certain variants the motors are equipped with a suitable encoder that for the rotor motor may be associated with the shaft, spindle or the rotary member, with preference for the last one.

The Use of the Innovative Detector Arrangement.

The use comprises a) determining the presence or the absence of a liquid and/or b) determining an uncharacterized feature of an analyte in at least one of the detection microcavities of a microfluidic disc, which is part of the rotary member of the arrangement described above.

The use corresponds to a method comprising the steps of:
i) providing the detection arrangement described above in which liquids have been introduced into one or more of the microchannel structures, and
ii) determining whether or not liquid has entered one or more predetermined detection microcavities, and/or if an analyte is present in one or more detection microcavities of the microchannel structures int which liquid has been introduced.

The SPR detector unit may also be used for proper matching/alignment the different parts of the rotary member to each other so that the incident beam can reach the SPR-surface and the reflected beam can reach the light-detecting subunit (LDS), or for keeping track of SPR-MCs that are in front of the SPR detector unit.

The liquid may be water or an organic solvent or a mixture of these kind of solvents. Typical liquids are aqueous. The analyte, i.e. the molecular entity to be detected by the SPR measurement, may be an affinity reactant which is capable of binding to an affinity counterpart that is immobilized to the SPR surface (inside the SPR-MCs). Also other analytes may be determined/monitored in the detection microcavities of the innovative arrangement provided the binding of the analyte to the SPR-surface changes the refractive index of the liquid next to the surface.

General Statement

Certain innovative aspects of the invention are defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A detector arrangement comprising:
   a) a rotary member having an axis of rotation, said member comprises:
      (i) one or more microfluidic discs, each disc comprises a plurality of essentially equal and enclosed microchannel structures which are designed for permitting liquid transport by centrifugal force created by spinning the disc around the axis of rotation, and a first plurality of surface plasmon resonance measuring cells (SPR-MCs), each SPR-MCs comprises a detection microcavity (DMC), wherein an SPR surface in an inner wall of the DMC and at least a part (P1) of a detection window (DW) that stretches from the SPR surface to an outer surface of the disc, and said outer surface of P1 for all SPR-MCs are at the same radial distances
      (ii) a rotatable disc holder comprising the remaining part (P2) of each of the DWs,
   b) a non-rotatable SPR detector comprising
      (i) a light source (LS), and
      (ii) a light detecting subunit (LDS),
   c) a beam path comprising
      (i) an incident beam path (ibp) going from LS to one of the SPR surfaces via the DW associated with this SPR surface, and
      (ii) a reflected beam path (rpb) going from the same SPR surface to LDS via said DW, the SPR-MCs being interchangeable by rotating said rotatory member.

2. The arrangement of claim 1, wherein each DW is fully integrated with each disc.

3. The arrangement of claim 1, wherein the DWs and the disc holder are present at the same side of the microfluidic disc.

4. The arrangement of claim 3, wherein
   (a) P1 and P2 of each of the DWs are connected to each other via an opto interface, and
   (b) ibp and rbp are capable of passing through both of said parts for each SPR-MC by rotating the rotary member.

5. The arrangement of claim 4, wherein said opto interface for each DW is present in an opto interface plate that is placed between the microfluidic disc and the disc holder.

6. The arrangement of claim 4, wherein
   (a) P2 for each DW is part of a separate plate that is a part of the disc holder, and
   (b) the disc is resting on top of this plate, said separate plate is made of glass.

7. The arrangement of claim 3, wherein ibp reaches and/or rpb path for each SPR-MC leaves the DW via one or more openings in the disc holder.

8. The detector arrangement of claim 1, wherein the DWs and the disc holder are on the opposite sides of the microfluidic disc.

9. The detector arrangement of claim 1, wherein said SPR detector and said rotary member are laterally movable relative to each other.

10. The arrangement of claim 9, wherein each microfluidic disc comprises a second plurality of SPR-MCs that are located at radial distances that are different from the radial distances of said first plurality.

11. The arrangement of claim 1, wherein the breadth of a light beam passing through the beam paths is less than the dimension of each of the SPR surfaces and its underlying detection chamber.

12. The arrangement claim 1, wherein at least a part of the SPR-MCs including the SPR surfaces and detection windows is arranged annularly as one or more concentric circles around the axis of symmetry.

13. The arrangement of claim 1, wherein at least a part of the SPR-MCs including the SPR surfaces and detection windows is in a spoke arrangement.

14. The arrangement of claim 1, wherein P1 for each of the DWs is made in plastic material having a refractive index within the range of 1.45-1.55.

15. The detector arrangement of claim 1, wherein each of the microcavities are part of a microchannel structure that may be the same or different for different microcavities.

16. The detector arrangement of claim 1, wherein the surfaces at the entrance and the exit for ibp and rpb, respectively, are essentially perpendicular to the optical axis of the incident and reflected light.

17. The detector arrangement of claim 1, wherein each DW is delineated by a prism surface at each of the entrance and exit of light.

18. The detector arrangement of claim 1, wherein subpressure retains the microfluidic disc in the disc holder.

* * * * *

UNITED STATES PATENT AND TRADEMARK OFFICE
CERTIFICATE OF CORRECTION

PATENT NO.        : 7,295,320 B2                                       Page 1 of 1
APPLICATION NO.   : 10/999532
DATED             : November 13, 2007
INVENTOR(S)       : Henrik Ostlin et al.

It is certified that error appears in the above-identified patent and that said Letters Patent is hereby corrected as shown below:

Title page item [73] should read
 Assignee: Gyros Patent AB, Uppsala (SE)

Signed and Sealed this
Twenty-first Day of June, 2011

David J. Kappos
*Director of the United States Patent and Trademark Office*